US00PP37072P3

(12) United States Plant Patent
Williams

(10) Patent No.: US PP37,072 P3
(45) Date of Patent: Oct. 28, 2025

(54) ***COLOCASIA* PLANT NAMED 'FLOCOPHADR'**

(50) Latin Name: ***Colocasia esculenta* (L.) Schott**
Varietal Denomination: FLOCOPHADR

(71) Applicant: Brian's Botanicals, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 0 days.

(21) Appl. No.: 18/831,293

(22) Filed: Oct. 18, 2024

(65) Prior Publication Data

US 2025/0133973 P1 Apr. 24, 2025

(30) Foreign Application Priority Data

Oct. 18, 2023 (QZ) ..... PBR 2023/2202

(51) Int. Cl.
*A01H 6/10* (2018.01)
*A01H 5/02* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — Samuel R McCoy, Jr.

(57) ABSTRACT

'FLOCOPHADR' is a distinctive *Colocasia* plant which is characterized by the combination of green petioles that are suffused with red-purple, laminas that are marbled with varying shades of green, with a light yellow-white color immediately adjacent to the veins which is itself narrowly margined yellow, light greyed-green foliar veins that are strongly suffused with red-purple at and near the union with the petiole, laminas that become progressively more concaved and incurved with age, and the stability of all characteristics from generation to generation.

3 Drawing Sheets

Latin name of the genus and species: The Latin name of the genus and species of the novel variety disclosed herein is *Colocasia esculenta* (L.) Schott.

Variety denomination: The inventive variety of *Colocasia* disclosed herein has been given the variety denomination 'FLOCOPHADR'.

CROSS REFERENCE TO RELATED APPLICATIONS

This application claims priority to the Community Plant Variety Rights application number 2023/2202, filed Oct. 18, 2023 which is herein incorporated by reference.

BACKGROUND OF THE INVENTION

The claimed plant originated as a seedling selection, resulting from the controlled pollination of an unnamed *Colocasia esculenta* seed parent (not patented) with a second unnamed *Colocasia esculenta* plant (not patented), the pollen parent. Both parents were developed and owned by the inventor and were never commercially released. The seed parent exhibits a unique strongly recurved foliage aspect while the pollen parent exhibits white foliar margins and a dark red petiole. The cross was performed by the inventor at a commercial greenhouse in Louisville, Kentucky in the summer of 2016. Seeds from said cross were harvested and germinated, and the resulting seedlings were grown to a mature size to evaluate each progeny for desirable commercial characteristics. In August of 2018, the inventor first observed one such plant that exhibited uniquely colored mid-green foliage with dark red veins and strongly recurved leaf margins. Upon confirmation of distinctness and stability of these characteristics, 'FLOCOPHADR' was selected for commercialization in August of 2021.

Asexual Reproduction: Asexual reproduction of 'FLOCOPHADR', by way of meristematic tissue culture, was first initiated in April of 2023 at a plant tissue culture laboratory in Nootdorp, The Netherlands. Through several subsequent generations of propagation there have been more than five hundred progenies produced which all maintain the unique features of the new plant.

SUMMARY OF THE INVENTION

The cultivar 'FLOCOPHADR' has not been observed under all possible environmental conditions. The phenotype may vary somewhat with variations in environment such as temperature, water availability, and light intensity, without, however, any variance in genotype. The following traits have been repeatedly observed and are determined to be the unique characteristics of 'FLOCOPHADR'. These characteristics in combination distinguish 'FLOCOPHADR' as a new and distinct *Colocasia* cultivar:

1. *Colocasia* 'FLOCOPHADR' exhibits laminas that are marbled with varying shades of green, with a light yellow-white color immediately adjacent to the veins which is itself narrowly margined yellow; and
2. *Colocasia* 'FLOCOPHADR' exhibits light greyed-green foliar veins that are strongly suffused with red-purple at and near the union with the petiole; and 3. *Colocasia* 'FLOCOPHADR' exhibits green petioles that are suffused with red-purple; and
4. *Colocasia* 'FLOCOPHADR' exhibits laminas that become progressively more concaved and incurved with age.

BOTANICAL DESCRIPTION OF THE PLANT

Figure 1:
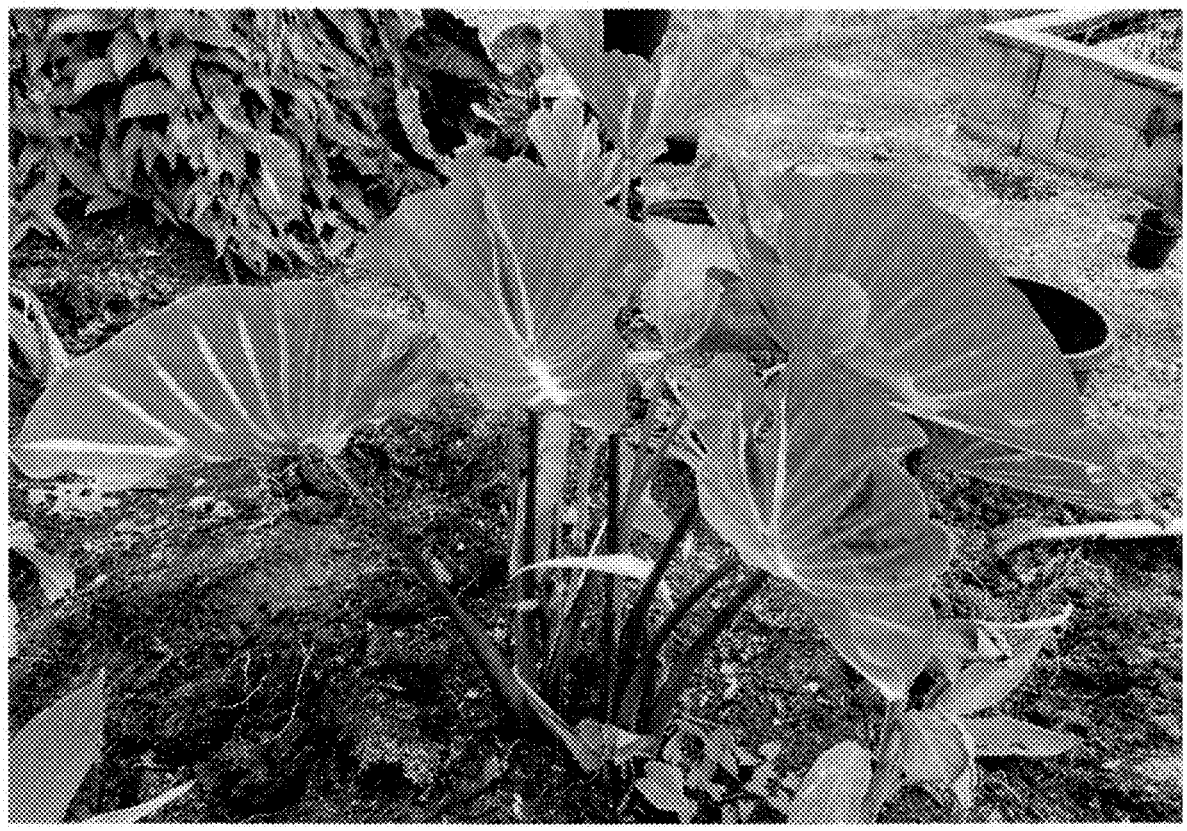
FIG. 1 illustrates, as nearly true as it is reasonably possible to make the same in color photographs of this type, an exemplary 12-month-old 'FLOCOPHADR' plant grown in a commercial greenhouse in Louisville, Kentucky.
Figure 2:
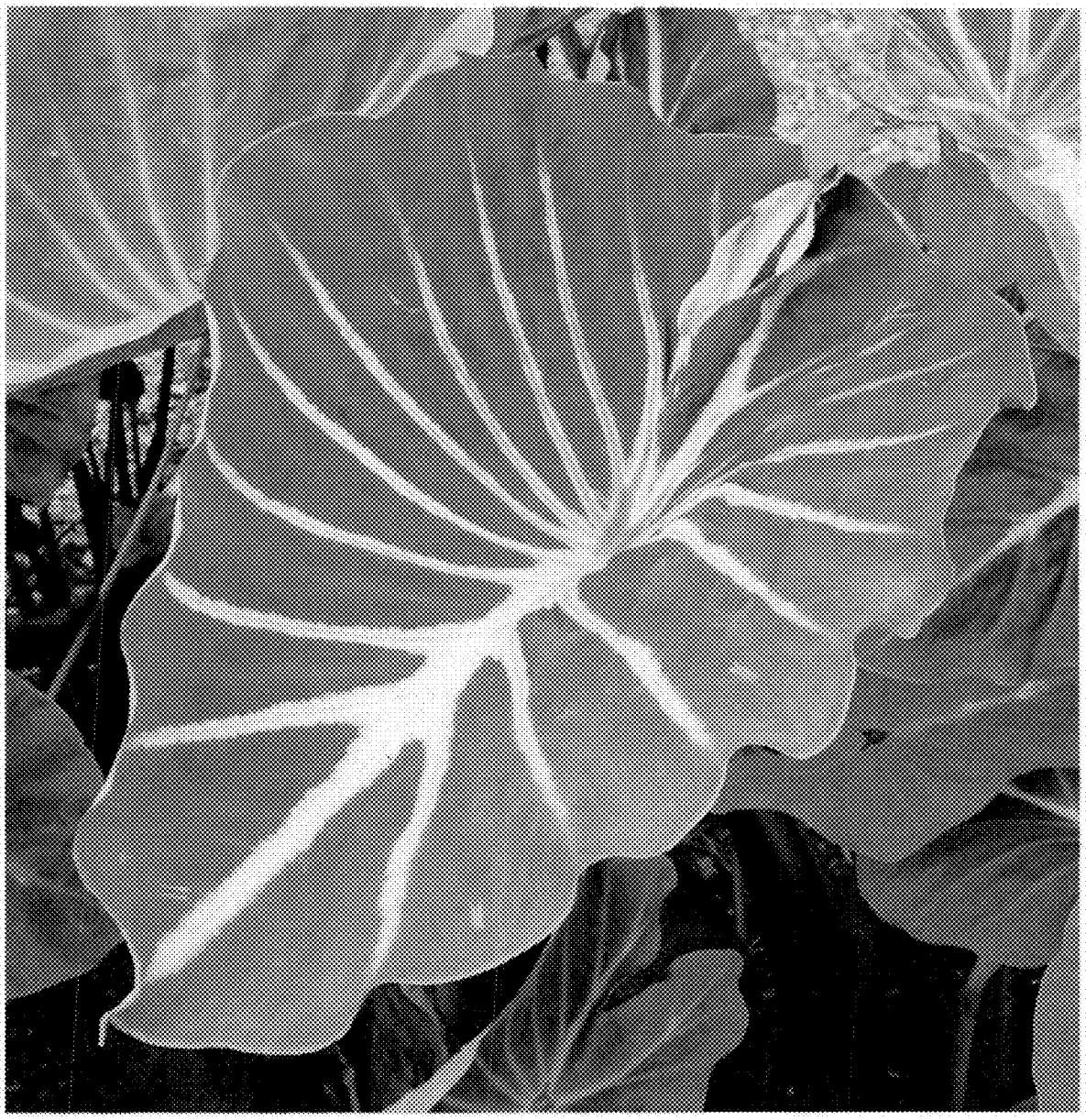
FIG. 2 illustrates, as nearly true as it is reasonably possible to make the same in color photographs of this type, the typical mature foliage of 'FLOCOPHADR'.
Figure 3:
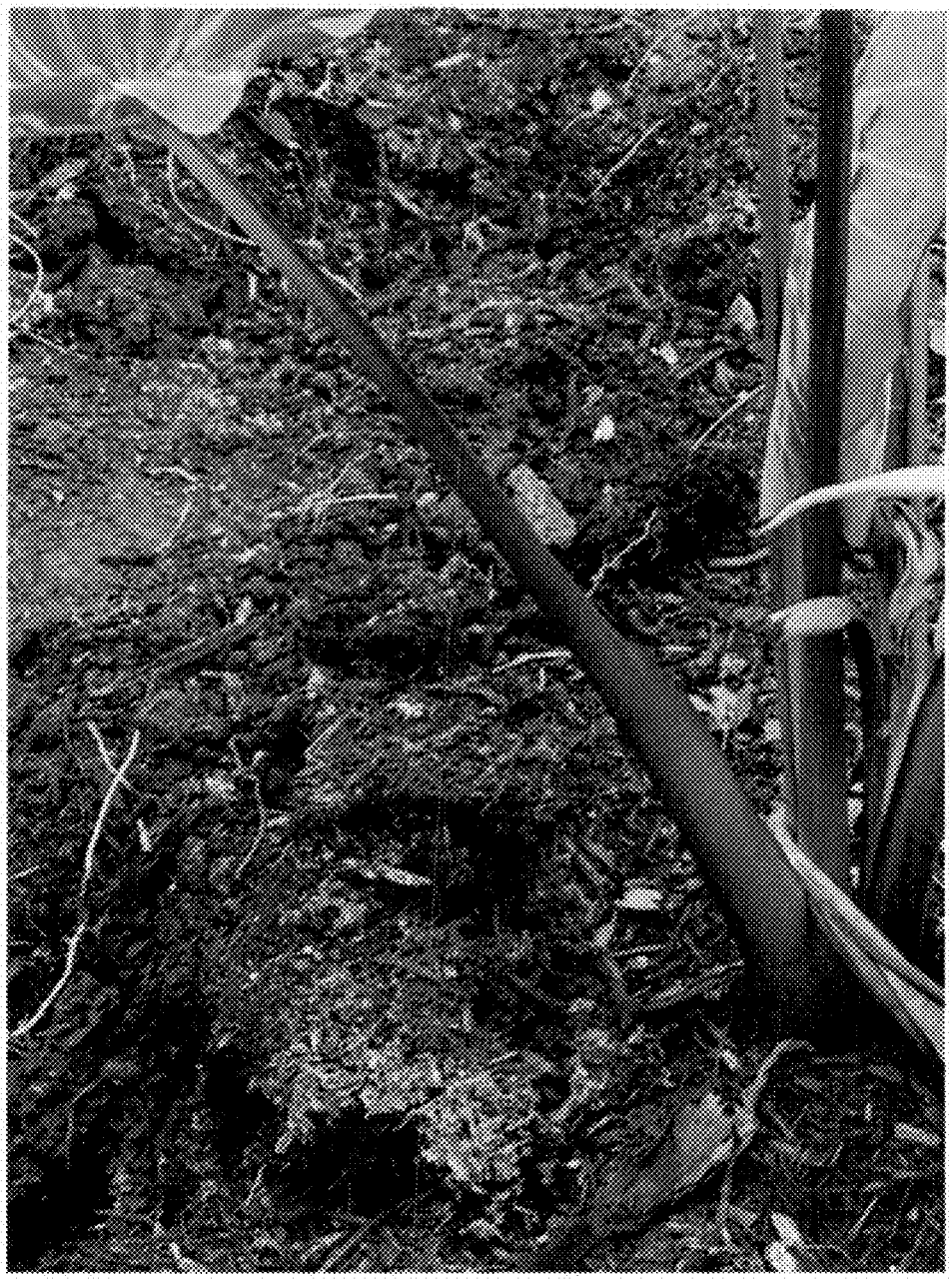
FIG. 3 illustrates, as nearly true as it is reasonably possible to make the same in color photographs of this type, the typical petiole of 'FLOCOPHADR'.

The following observations and measurements made in October of 2024 describe the approximations of a 12-month-old 'FLOCOPHADR' plant grown in a 25 cm nursery container at a greenhouse in South Carolina, United States. The plant was produced in a climate-controlled greenhouse with 35 percent shade covering and was maintained with regular overhead irrigation, slow-release granular fertilizer with a complete analysis, curative chemical pest control measures to control aphids and spider mites, and preventative fungicide applications.

Those skilled in the art will appreciate that certain characteristics will vary with older or, conversely, with younger plants. 'FLOCOPHADR' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Second Edition.

A botanical description of 'FLOCOPHADR' and comparisons with the parent plants and most similar commercial comparator are provided below.

General plant description:

*Growth habit*.—Clumping herbaceous perennial; acaulescent, with foliage arising directly from the base of each clump.

*Plant growth habit profile*.—Vase-shaped.

*Height*.—Approximately 215 cm.

*Width*.—Average 150 cm.

*Growth rate*.—Fast growing.

*Plant vigor*.—Moderately to highly vigorous.

*Propagation*.—Method — Meristematic tissue culture. Time to initiate roots — Approximately 2 to 5 weeks to initiate roots at an average ambient temperature of 29.4 degrees Celsius. Crop time — Approximately 3 to 5 weeks to produce a well-rooted, marketable 10 cm container from a rooted cutting.

*Environmental tolerances*.—Moderately high tolerance to rain; moderate tolerance to wind; not drought tolerant; tolerant of temperatures to at least 40 degrees Celsius. Cold hardy to USDA Hardiness Zone 8.

*Pest resistance and susceptibility*.—Plants have not been observed to be any more or less susceptible or resistant to *Phytophthora* sp. and *Pythium* sp. pathogens and spider mite (*Tetranychus* sp.) and aphid (*Aphididae*) insect pests when compared to the common form of the species, *Colocasia esculenta*.

Root system:

*General*.—*Colocasia* sp. exhibits a shallow root system with fleshy adventitious roots arising from large fusiform corms; corms bearing non-detachable obovate cormels.

*Branching*.—Freely branched.

*Density*.—Moderately dense.

*Distribution*.—Relatively shallow.

*Texture*.—Fleshy; smooth; lacking root hairs.

Stems:

*Branching characteristics*.—*Colocasia* sp. is acaulescent; no stems or lateral branches are produced.

Foliage:

*Arrangement*.—Basal foliage is alternate to spiraled.

*Division*.—Simple.

*Attachment*.—Petiolate; peltate.

*Quantity of leaves per shoot*.—18.

*Lamina*.—Shape — Narrowly cordate. Apex — Acuminate. Base — Cordate. Aspect — Concave; incurved. Attitude — Leaves emerge in the same plane as the petiole yet mature to oblique or pendulous. Dimensions — Approximately 75.0 cm long and 60.0 cm wide at maturity. Margin — Entire; strongly undulated; curling into a convex shape around petiole. Texture and luster, adaxial and abaxial surfaces — Strongly rugose, glabrous, velvety, matte, and moderately to strongly glaucous. Juvenile color, adaxial surface — Green, a combination of RHS 139A and 141A; margins are suffused with green, nearest to RHS 143B. Juvenile color, abaxial surface — Green, closest to 143B. Mature color, adaxial surface — Marbled with a combination of varying shades of green, nearest to RHS 135A, 143C, and 144B; the laminar surface immediately adjacent to the veins is colored yellow-white, nearest to a combination of RHS 158B and 158C; the yellow-white coloration is narrowly margined yellow, nearest to a combination of RHS 9C and 10B. Mature color, abaxial surface — Green, nearest to RHS 143B; the laminar surface immediately adjacent to the veins is colored yellow combination of RHS 9C and 10B. Venation — Vein pattern — Pinnate; venation is very prominent and is raised on the abaxial laminar surface. Vein color, adaxial surface — Greyed-green, nearest to RHS 194B; and strongly suffused with red-purple at the point of union with the petiole, nearest to a combination of RHS 72B and 75A. Vein color, abaxial surface — Greyed-green, nearest to RHS 194B, and slightly glaucescent.

*Petiole*.—Attachment — Sheathed. Aspect — Terete. Length — Approximately 87 cm. Width — Approximately 2.2 cm, including the petiole wings, at the proximal end and 0.4 cm at the distal end. Strength — Moderately strong. Texture — Smooth and glabrous. Luster — Matte to very slightly glossy. Color — Green, nearest to RHS 143B with moderate to strong red-purple suffusion, nearest to a combination of RHS 72B and 75A. Petiole wings —

General Description — Two petiole wings extend to about one-third of the length of the petiole; wings clasped. Length — Approximately 7.6 cm. Width — Approximately 1.25 cm at the base. Margins — Entire. Texture and luster — Glabrous and very slightly glossy. Color — Green, nearest to RHS 143B with red-purple edges nearest to a combination of RHS 72B and 75A.

Inflorescence: *Colocasia* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: No seeds or fruit have been observed to date.

COMPARISONS WITH THE PARENT PLANTS

Plants of the new cultivar 'FLOCOPHADR' differ from the seed parent, an unnamed *Colocasia esculenta* plant (not patented), in the characteristics described in Table 1 below.

TABLE 1

| Characteristic | 'FLOCOPHADR' | The seed parent |
|---|---|---|
| General coloration of the petioles. | Green and strongly suffused with red-purple. | Green. |
| General coloration of the mature foliage. | Marbled with varying shades of green, with light greyed-green veins, and a yellow-white color immediately adjacent to the veins, and a yellow-white coloration immediately adjacent to the veins which is itself narrowly margined yellow. | Green with white veins and a small star-shaped blotch in the central zone of the lamina. |
| General coloration of foliar veins. | White main and lateral veins; the main vein is strongly suffused with red-porple at the union with the petiole. | White main and lateral veins. |
| Foliage aspect. | Concaved; incorved. | Pendulous; recurved. |

Plants of the new cultivar 'FLOCOPHADR' differ from the pollen parent, an unnamed *Colocasia esculenta* plant (not patented), in the characteristics described in Table 2 below.

TABLE 2

| Characteristic | 'FLOCOPHADR' | The pollen parent |
|---|---|---|
| General coloration of the petioles. | Green and strongly suffused with red-purple. | Green with light pink suffusion. |
| General coloration of the mature foliage. | Marbled with varying shades of green, with light greyed-green veins, and a yellow-white coloration immediately adjacent to the veins which is itself narrowly margined yellow. Veins are strongly suffused with red-purple at and near the union with the petiole. | Green with a white main vein; lateral veins are indistinguishable from the surrounding foliage. |
| Foliage aspect. | More concaved and incurved at all stages of development. | Laminas become more concaved and incurved with age. |

COMPARISONS WITH THE CLOSEST KNOWN COMPARATOR

Plants of the new cultivar 'FLOCOPHADR' differ from the closest known commercial comparator, *Colocasia* sp. 'Black Magic' (not patented) in the following characteristics described in Table 3 below.

TABLE 3

| Characteristic | 'FLOCOPHADR' | 'Black Magic' |
|---|---|---|
| General coloration of the petioles. | Green and strongly suffused with red-purple. | Dark maroon. |
| General coloration of the mature foliage. | Marbled with varying shades of green, with light greyed-green veins, and a yellow-white coloration immediately adjacent to the veins which is itself narrowly margined yellow. Veins are strongly suffused with red-purple at and near the union with the petiole. | Dark near-black foliage. |
| Foliage aspect. | Concaved; incurved. | Pendulous; recurved. |

That which is claimed is:

1. A new and distinct variety of *Colocasia* plant named 'FLOCOPHADR', substantially as described and illustrated herein.

* * * * *